United States Patent [19]

Akutsu et al.

[11] 3,958,128

[45] May 18, 1976

[54] SYSTEM FOR DETERMINING A TRANSVERSAL POSITION OF ANY DEFECT IN A TRAVELING SHEET MATERIAL

[75] Inventors: Shoji Akutsu; Yasumasa Watanabe; Yasuhiko Mashino, all of Chiba; Tomohiro Chaki; Masakazu Fujita, both of Tokyo, all of Japan

[73] Assignees: Kawasaki Steel Corporation; Toei Denshi Kogyo Kabushiki Kaisha, both of Japan

[22] Filed: Sept. 24, 1974

[21] Appl. No.: 508,802

[30] Foreign Application Priority Data

Sept. 28, 1973 Japan.............................. 48-108543
Sept. 28, 1973 Japan.............................. 48-108544

[52] U.S. Cl............................... 250/563; 250/572; 250/578; 356/200

[51] Int. Cl.² ......................................... G01N 21/32
[58] Field of Search ........... 250/559, 561, 562, 563, 250/571, 572, 578; 356/200

[56] References Cited
UNITED STATES PATENTS

| 3,556,664 | 1/1971 | Blaisdell et al. ................ 250/571 X |
| 3,825,765 | 7/1974 | Schober et al...................... 250/563 |

*Primary Examiner*—Alfred E. Smith
*Assistant Examiner*—E. R. LaRoche
*Attorney, Agent, or Firm*—Henry R. Lerner

[57] ABSTRACT

A system for determining a transversal position of any defect in a traveling sheet material having a defect detector and at least one scanning detector, in which the transversal position of the defect in the sheet material is determined by the coincidence between a defect signal from the defect detector and an output signal from the scanning detector.

3 Claims, 6 Drawing Figures

FIG. 1
FIG. 2
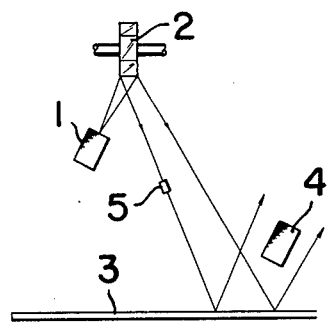
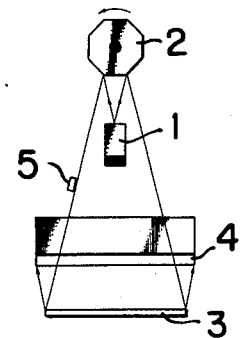
FIG. 3
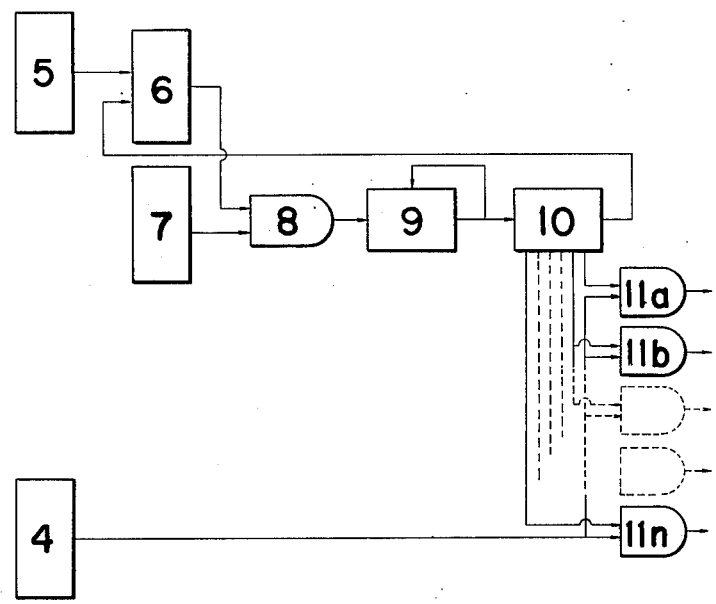

SYSTEM FOR DETERMINING A TRANSVERSAL POSITION OF ANY DEFECT IN A TRAVELING SHEET MATERIAL

The present invention relates to a system for determining a transversal position of any defect in a traveling sheet material, which position may be between the opposite edges of the sheet material.

It has been proposed to project a scanning light beam onto a surface of a traveling sheet material such as steel or non-ferrous metal plate, paper or film and the like and to use a photoelectric converter to detect as a defect signal a variation of light quantity in a light beam due to any defect when the projected light beam is reflected from or transmitted through the material, said defect signal being used to determine a defect position. In such case, there are available two types of defect photodetecting elements; one of them is a scanning type detector while the other is a fixed type detector. With the former, a rectangular light image of a light source is scanned in a direction at right angles with respect to the traveling direction of the sheet material and the variation in a reflected light quantity of the light beam is converted by a detecting element of the photodetector into an electrical signal. In this case, a plurality of photodetectors are arranged as overlapped to one another to compensate the difference in sensitivity between the central and edge portions, since the distance of light scanning becomes longer with displacement from the center of the surface of sheet material to be inspected. In a system using a fixed type detector, an illuminator and photodetectors are so arranged in a row across the length of the sheet material to be inspected such that the light from the illuminator, that is a spot-illuminating light source, is projected onto the surface of the sheet material to be inspected. The light is projected at right angles with respect to the direction of movement of the material, and the reflected light from the surface is received by the photodetector element through a slit, the view field of which photodetector is sectionalized in the transverse direction.

In either case, the identification of the transversal position of any defect in the sheet material is not achieved. But, recently it has become necessary to inspect a sheet material and locate the defect. This is because any slight defect in the portion of a material to be welded, such as an plate for pipe will be a great problem, since such defect may lead to poor welding or damage of the welder electrodes, although such slight defect would not cause problems for the plate to be pressed since the defective portion may be removed.

In the foregoing, the weighting of the opposite edge portions of a material has been described. Also it has become necessary to weight in the transversal direction portions other than such opposite edge portions. For example, when a steel plate has any flaw caused by friction between one plate and another, it is convenient for the operational purposes to know the manufacturing process and the manner in which the flaw took place.

The invention therefore seeks to provide a system for determining the transversal position of any defect in a traveling sheet material having a defect detector and at least one scanning detector, in which the transversal position of the defect in the sheet material is determined by coincidence of output signals from both the detectors.

According to one feature of the present invention, a scanning detector is so arranged between the light source and the sheet material that it partly receives a scanning light beam that is emitted from a light source and is reflected onto a reflector before arriving at one surface of the sheet material. The output signal derived from said scanning detector when it receives the light beam, is fed to a sectionalizing means to produce preset count or section signals. Each of the said section signals is compared for coincidence with the defect signal from the defect detector device in order to determine the transversal position of the defect in the sheet material.

According to another feature of the invention, a plurality of scanning detectors are provided at selected intervals transversally between the light source and the sheet material to be inspected to produce section signals which are used for the determination of the defect position in the sheet material.

Said reflector may be in the form of a rotating multi-surface mirror having, for example, 8 or 16 surfaces.

Each of the defect detector and the scanning detector may be respectively constructed by a suitable photoelectric converter such as photocell or photodiode.

For a better understanding of the invention and to show how the same may be carried into effect, reference will be made to the accompanying drawings, in which:

FIGS. 1 and 2 are a side view and a front view, respectively, which show one embodiment of the system according to the present invention;

FIG. 3 is a block diagram showing a circuit arrangement for processing the output signals from the defect detector and the scanning detector shown in FIGS. 1 and 2;

Figure 4:
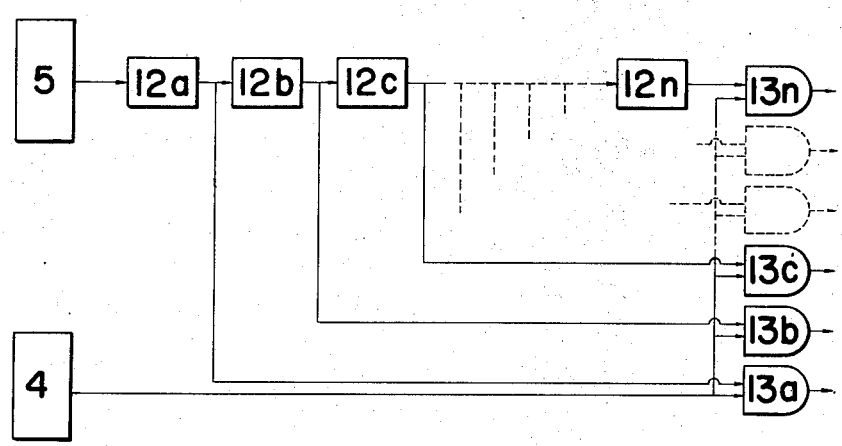
FIG. 4 is a block diagram showing a modification of the circuit arrangement of FIG. 3.

Refering now to FIGS. 1 and 2, which are schematic diagrams, respectively, of one embodiment of the system according to the present invention, a light source 1 emits a light beam which is reflected by a rotating multi-surface mirror such as an eight-surface mirror 2 and is projected onto a traveling sheet material 3 which is to be inspected. A defect detector means 4 is arranged to receive the reflected light beam from the surface of the material 3. The light beam is varied in light quantity at the time of reflection by the surface of the sheet material 3 if there is any defect in the surface of said material 3. Thus, the defect detector means 4 generates the defect signal, which is converted into a pulse signal in response to the variation in the light quantity due to the defect. The rotating speed of the mirror 2 may be selected in connection with the running speed and width of the sheet material 3, and the driving means for the mirror 2 is not shown in the drawing.

In this embodiment of the present invention, a scanning detector means 5 is provided to receive the light beam emitted toward the sheet material 3 just before it arrives at the one edge of the material 3 and to produce the scanning zone signal, the sequential light beam being reflected from the surface of the sheet material 3 and received by the defect detector means 4.

If the material to be inspected is transparent such as film, any transmitted light beam may be used instead of the reflected light beam. In such case, the defect detector may be located on the opposite side of the material to be inspected.

FIGS. 3 and 4 show two ways how the output signals of the defect and scanning detector means may be processed.

FIG. 3 shows a circuit arrangement using a counter circuit as the sectionalizing means. The scanning zone signal produced by the scanning detector means 5 is fed to a flip-flop 6. Reference 7 numeral denotes a pulse oscillator. The output of the flip-flop 6 is connected to an AND circuit 8 which is also supplied with the pulse output from the oscillator 7. The AND circuit 8 is connected to a first preset counter 9 which in turn starts counting by the output pulse from the AND circuit 8 and continues to count until a preset value is achieved. Then, the counter 9 delivers predetermined output pulse at a set count and is reset to start the counting again. The output pulse is fed to a second preset counter 10 where the pulse is counted. Similarly, the second counter 10 is reset when it counts up to a certain preset value. Thus, one scanning cycle is completed. Consequently, the numerical value provided from the second counter 10 represent the transversal sections of the sheet material 3. The outputs of the second counter 10 are respectively connected to one input of each of n AND circuits 11a, 11b, ... 11n, each of which has the other input connected to the output of the defect detector means 4. Therefore, the numerical signals from the second counter 10 and the output signal or defect signal from the defect detection means 4 are applied to the AND circuits 11a to 11n. From the AND circuit where said signals are compared for coincidence, is provided the pulse output if there is the coincidence between said signals. This pulse output may be utilized to identify the transversal position of the defect in the sheet material 3.

FIG. 4 shows an alternate circuit arrangement using monostable multivibrators as the sectionalizing means, n monostable multivibrators 12a, 12b, 12c, ... 12n which are connected in series to each other are provided to divide or sectionalize one zone into n scanning sections. The scanning light beam from the rotating mirror 2 shown in FIGS. 1 and 2 is partly detected by the scanning detector means 5 and photoelectrically converted into an electrical signal which is fed to and operates the first monostable circuit 12a. The monostable circuit 12a forms the first section signal which in turn is fed to the second monostable circuit 12b. The monostable circuit 12b will be operated at the end of the first section, which forms the second section signal. Subsequently, the monostable circuit 12c to 12n sequentially form the 3rd to n-th section signals, in similar manner. Such signals of sections are respectively fed to one input of each of n AND circuits 13a, 13b, ... 13n, while other input of each AND circuit is supplied with the output representing the defect detection from the defect detector means 4 shown in FIGS. 1 and 2. In each of said AND circuits 13a to 13n, a comparison is made for coincidence between the section and the defect signals. When the outputs coincide, the output signal may be obtained for determining the transversal position of the defect in the sheet material by taking the output out of the AND circuit in question.

As seen in the foregoing, the counter circuit in FIG. 3 and the monostable multivibrator circuit in FIG. 4 are started at the beginning of scanning the material to be inspected, and thereafter the transversal position of the defect in the material can be determined using a regular time interval which corresponds to an interval of distance. It is appreciated that various similar counting means may be used.

Figure 5:
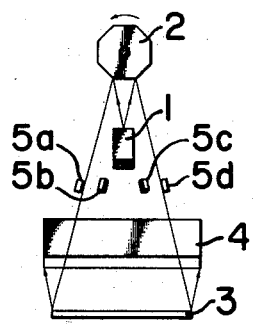
FIG. 5 is a front view of another embodiment of the present invention.

FIG. 5 show another embodiment according to the present invention. In the same way as the preceding embodiment shown in FIGS. 1 and 2, the light source 1 emits a light beam which is reflected by the rotating multi-surface mirror 2 and is projected onto the traveling sheet material 3 which is to be inspected. The defect detector 4 is arranged to receive the reflected light beam from the surface of the material 3. The light beam may be varied in light quantity if there is any defect in the surface. Thus, the defect detector 4 generates the defect signal in response to the variation in the light quantity due to the defect.

Further, in the embodiment shown in FIG. 5, four photodetecting means 5a, 5b, 5c and 5d are disposed at an appropriate interval spacing between the rotating mirror 2 and the sheet material 3 before the light arrives at the sheet material 3. The light beam is detected first by the first detector 5a, then by the second and the third detectors 5b and 5c and finally detected by the last detector 5d during the time when the scanning of the light beam on the sheet material is proceeding.

Now, the operation of the transversal scanning detectors 5a to 5d will be further described in the following.

Figure 6:
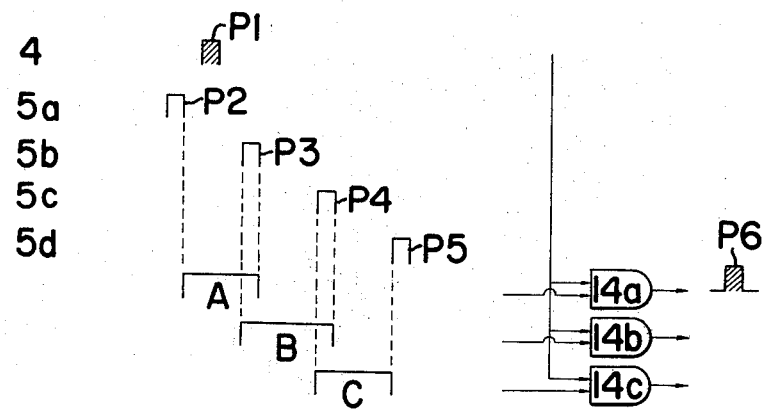
FIG. 6 is a block diagram of a circuit arrangement for the system shown in FIG. 5.

The light beam reflected from the rotating mirror 2 is partly detected first by the scanning detector 5a while the other part of the light beam is forwarded toward and reflected by the sheet material 3, and then detected by the defect detector 4. Further, the light beam is forwarded in the direction transversing the sheet material 3, through the scanning detectors 5b and 5c to the scanning detector 5d. As shown in FIG. 6, which shows a circuit arrangement for the apparatus shown in FIG. 5, the interval from the end of the first detector 5a to that of the detector 5b may be taken as section "A," the interval from the beginning of the detector 5b to the end of the detector 5c is as section "B," and the interval from the beginning of the detector 5c to that of the detector 5d is taken as section "C." Therefore, those section signals and the defect signal from the defect detector 4 are compared for coincidence to determine the transversal position of the defect. As seen in FIG. 6, for example, the defect signal "P1" appears in the section "A."

Also in FIG. 6, there are provided AND circuits 14a, 14b and 14c so that comparison is made for coincidence between the signals from the section "A" and the defect detector 4, from the section "B" and the detector 4, and from the section "C" and the detector 4, respectively. In the case of FIG. 6, the pulse waveform "P6" is derived from the AND circuit 14a for the coincidence between the signals from the section "A" and the detector 4, and used in determining the transversal position of the defect.

Also in FIG. 6, the waveform "P1" is for the defect signal from the defect detector 4, waveforms "P2" to "P5" are for the section signals of the respective scanning detectors 5a to 5d, since in the embodiment shown in FIG. 6, a plurality of scanning detectors 5a to 5d are used.

It is appreciated that a plurality of scanning detectors may be disposed with narrow intervals mainly on the edge portions and the discrimination level can be set arbitrarily so that the inspection may be made possible on the edge portions independently of the central portion of the sheet material, which permits more economical discrimination of the flaw on the edge portions.

As have been described in the foregoing, the present invention determines optically the transversal position of any defect in a traveling sheet material, using the scanning detector(s) in addition to the defect photodetecting means, which provides improvement in the manufacturing process control and productivity.

The foregoing description of the preferred embodiments of the invention is given here by way of example only. The invention is not to be taken as limited to any of the specific features as described, but comprehends all such variations as come within the scope of the appended claims.

What is claimed is:

1. A system for determining the transversal position of any defect in a traveling sheet material, comprising means for projecting a scanning light beam onto one side of the traveling sheet material to be inspected, means for detecting a defect in the sheet material which is arranged to receive the reflected scanning light beam from the material and to generate a defect signal when there is a defect in the sheet material, and means for detecting a scanning zone in the sheet material, said means for detecting a scanning zone being arranged between the light source and the said sheet material to receive partly the scanning light beam before said light beam impinges on said one surface of sheet material and to generate an output signal for the determination of the scanning zone, the transversal position of the defect in the material being determined by the coincidence between a defect signal from said defect detector means and the output signal from the said scanning detecting means.

2. A system for determining the transversal position of any defect in a traveling sheet material, comprising means for projecting a scanning light beam onto one side of a sheet material to be inspected, means for detecting the defect in the sheet material which is arranged to receive the reflected scanning light beam from the sheet material and to generate a defect signal when there is the defect in the sheet material, a plurality of scanning detecting means being provided at selected intervals transversally between the light source and the said sheet material to receive partly the scanning light beam before said scanning light beam impinges onto said one surface of sheet material and to generate respective output signals to form respective scanning zones in the sheet material, and means for sectionalizing the scanning zones into a number of sections, said means for sectionalizing being connected to the outputs of said scanning detecting means, the transversal position of the defect in the sheet material being determined by coincidence between a defect signal from said defect detector means and the section signals from said sectionalizing means.

3. A system for determining the transversal position of any defect in a traveling material, comprising: means for projecting a scanning light beam onto one side of the sheet material to be inspected, means for detecting the defect in the material which is arranged to receive the reflected light beam from the material and to generate a defect signal when there is the defect in the sheet material, means for detecting a scanning zone being arranged between the light source and the said sheet material to receive partly the scanning light beam before said light beam impinges at one edge of the sheet material and to generate an output signal for the determination of the scanning zone, and electrical means for sectionalizing the scanning zone into a number of sections which is connected to the output of said scanning detector means, said electrical means comprising a plurality of mono-stable multivibrators connected in series, the transversal position of the defect in the sheet material being determined by a coincidence between the defect signal from said defect detector means and the scanning section signals produced by said electrical means.

* * * * *